United States Patent [19]
Wallace et al.

[11] Patent Number: 5,352,715
[45] Date of Patent: Oct. 4, 1994

[54] INJECTABLE CERAMIC COMPOSITIONS AND METHODS FOR THEIR PREPARATION AND USE

[75] Inventors: Donald G. Wallace, Menlo Park; Hugh McMullin, Pacifica; George Chu, Cupertino, all of Calif.

[73] Assignee: Collagen Corporation, Palo Alto, Calif.

[21] Appl. No.: 101,333

[22] Filed: Aug. 2, 1993

Related U.S. Application Data

[63] Continuation of Ser. No. 843,646, Feb. 28, 1992, abandoned.

[51] Int. Cl.$^5$ .............. A61F 2/00; C08K 3/32; A61M 31/00
[52] U.S. Cl. .................... 523/115; 523/113; 524/415; 524/417; 604/56; 424/423
[58] Field of Search ............... 523/113, 115; 524/415, 524/417; 604/56; 424/423

[56] References Cited

U.S. PATENT DOCUMENTS

| | | | |
|---|---|---|---|
| 4,563,350 | 1/1986 | Nathan et al. | 424/95 |
| 4,684,673 | 8/1987 | Adachi | 523/115 |
| 4,776,890 | 10/1988 | Chu | 106/161 |
| 4,795,467 | 1/1989 | Piez et al. | 623/16 |
| 4,803,075 | 2/1989 | Wallace et al. | 424/423 |
| 4,842,603 | 6/1989 | Draenert | 523/115 |
| 4,863,732 | 9/1989 | Nathan et al. | 424/95 |
| 4,865,602 | 9/1989 | Smestad et al. | 623/16 |
| 4,992,226 | 2/1991 | Piez et al. | 264/109 |
| 5,001,169 | 3/1991 | Nathan et al. | 523/113 |

OTHER PUBLICATIONS

Lemons et al. Second World Congress of Biomaterials, Apr. 27-May 1, 1984.
Polytef® Paste (Mentor Corporation, Santa Barbara, Calif.) 2 page description.
Hench, "Bioglass Implants for otology," in: *Biomaterials in Otology*, Grote, ed., pp. 62–69, Martinus Nijhoff Publ. (1983).

*Primary Examiner*—Paul R. Michl
*Assistant Examiner*—LaVonda DeWitt
*Attorney, Agent, or Firm*—Townsend and Townsend Khourie and Crew

[57] ABSTRACT

Injectable implant compositions comprise a biocompatible ceramic matrix present in a fluid carrier, where the ceramic matrix comprises particles having a size distribution in the range from 50 μm to 250 μm. Optionally, the compositions may further comprise collagen, where the relative amounts of collagen and ceramic matrix at least partly determine the physical properties of implants formed by injecting the compositions. The fluid carrier is an aqueous buffered medium, typically including an organic polymer base material when there is no collagen present in the composition. The compositions are particularly suitable for repair and augmentation of soft and hard tissues by injection.

37 Claims, 1 Drawing Sheet

INJECTABLE CERAMIC COMPOSITIONS AND METHODS FOR THEIR PREPARATION AND USE

This is a continuation of application Ser. No. 07/843,646 filed Feb. 28, 1992, now abandoned.

BACKGROUND OF THE INVENTION

1. Field of the Invention

The present invention relates generally to the preparation and use of biocompatible implant compositions. More particularly, the present invention relates to injectable ceramic implant compositions for soft and hard tissue repair and augmentation.

The use of collagen compositions for tissue repair and augmentation is known. The collagen may be utilized in a variety of forms, including cross-linked and non-cross-linked fibrillar collagens, gelatins, and the like, and may be combined with various other components, such as lubricants, osteogenic factors, ceramic particles, and the like, depending on the intended use. For soft tissue repair, suspensions of fibrillar collagen have often been used by injecting the composition to a treatment site through a fine gauge needle. For bone and hard tissue repair, fibrillar collagens have been combined with the ceramic powders, such as hydroxyapatite and other calcium phosphates. These compositions, however, have not been injectable.

The use of fibrillar collagen as the primary matrix material in injectable soft and hard tissue implant compositions has several limitations. The preparation of fibrillar collagen suitable for human use is relatively time consuming and expensive. In particular, the complete removal of contaminating and potentially immunogenic substances to produce "atelocollagen" is a relatively complex and expensive procedure. Moreover, the persistence, shape retention, cohesiveness, stability, elasticity, toughness, and intrudability of the fibrillar collagen compositions could be improved.

Heretofore, fibrillar and other collagens have been used primarily for superficial soft tissue augmentation, i.e., near the surface of the skin. For deep tissue injection, particularly to locations near bone and cartilage, the use of cross-linked collagens is problematic, and the use of non-cross-linked collagens is ineffective.

One approach for improving the compositions utilized for soft and hard tissue repair and augmentation would be to at least partly replace the fibrillar collagen in such formulations with a ceramic mineral material, particularly with hydroxyapatite or other calcium phosphate minerals. Hydroxyapatite has very low immunogenicity.

The incorporation of such mineral particles in compositions intended for soft and hard tissue treatment, however, has been found to be ineffective due to the difficulty in introducing such compositions to the treatment site. In particular, the incorporation of generally available ceramic mineral particles inhibits or prevents the introduction of the compositions through a fine gauge needle to the tissue site of interest. Thus, injectable ceramic implant materials have generally not been available and any benefits which may derive from their use remain speculative.

It would therefore be desirable to provide improved injectable implant materials for soft and hard tissue repair and augmentation where at least a portion of the primary tissue matrix substance is a biocompatible ceramic material. Such compositions should be readily injectable so that they can be introduced to a desired soft tissue site using a fine gauge needle. In addition, such compositions should be persistent at the site of injection, preferably adhering to the soft tissue into which they have been injected; they should be stable, i.e. undergo no significant changes in situ; be tough and elastic, i.e. be capable of bearing loads without undergoing excessive or permanent deformation; be non-toxic and well-tolerated by the body, i.e., produce no or tolerable levels of immune and inflammatory responses; and be intrudable, i.e., form a relatively dispersed, irregularly shaped mass within the tissue where the composition has been introduced. In particular, the improved implant materials should be suitable for deep tissue injection, particularly to locations near bone and cartilage, for purposes such as sphincter repair, nasal repair, and the like. It will be appreciated, of course, that the compositions and methods of the present invention while meeting at least some of these objectives, will not necessarily meet each of these objectives in every embodiment.

2. Description of the Background Art

Compositions comprising collagen and a mineral material, such as hydroxyapatite or tricalcium phosphate, are known for use in repairing bone defects. See, for example, U.S. Pat. Nos. 5,001,169; 4,992,226 (which is a division of U.S. Pat. No. 4,795,467); 4,865,602; 4,776,890; and 4,563,350. Lemons et al. Second World Congress of Biomaterials, Apr. 27–May 1, 1984, reported the use of collagen and hydroxyapatite/calcium phosphate compositions to repair bone lesions in rabbits. A soon to be commercially available composition with the trade name COLLAGRAFT (Zimmer, Inc., Warsaw, Ind.) comprises highly purified bovine dermal collagen which is combined with hydroxyapatite and tricalcium phosphate at a ratio of about 1:15 collagen: ceramic by dry weight. Such collagen and mineral formulations are generally not injectable through a small diameter needle and have not been employed for soft tissue repair.

U.S. Pat. No. 4,803,075, describes collagen compositions including a lubricant material to enhance injectability through narrow diameter needles for soft tissue repair. U.S. Pat. No. 4,863,732, describes an injectable composition comprising collagen and an osteogenic factor suitable for bone repair. POLYTEF ® Paste (Mentor Corporation, Santa Barbara, Calif.) is an injectable paste composition comprising pyrolyzed poly(tetrafluroethylene) particles present in glycerin with a small amount of polysorbate 20 suitable for tissue repair of the larynx.

Hydroxyapatite layers on various surgical implants have been found to enhance bonding to soft tissue in a host. Hence, "Bioglass Implants for Otology," in: *Biomaterials in Otology*, Grote, ed., pp. 62–69, Martinus Nijhoff Publishers, The Hague (1983).

The full disclosures of each of these references are incorporated herein by reference.

SUMMARY OF THE INVENTION

The present invention comprises injectable implant compositions which incorporate biocompatible ceramic particles as a primary matrix material. The ceramic matrix particles are sized within a range selected to enhance injectability and minimize immune and inflammatory response and are present in a pharmaceutically acceptable fluid carrier, typically an aqueous media which optionally includes an organic polymer to form a gel for suspending the ceramic particles. Compositions may further comprise fibrillar collagen as a co-matrix material, where the ratio of ceramic matrix to collagen matrix is selected to provide for a desired consistency or firmness in the resulting implant.

The use of biocompatible ceramic particles as a primary matrix is advantageous in a number of respects. The ceramic particles are able to become anchored within a host's own tissue, resulting in a very persistent implant which remains stable over extended time periods. Despite this ability to interact with the host tissue, the ceramic matrix particles are substantially immunologically inert and cause little or no immune or inflammatory response. Further, by selecting resorbable or inert (non-resorbable) ceramic materials, or combinations thereof, the long-term persistence of the implant can be programmed depending on the particular application. Additionally, the ceramic matrix materials are inexpensive relative to other matrix materials, such as collagen, thus reducing the cost of the compositions of the present invention. Moreover, by employing collagen as a co-matrix material, soft tissue implants having a wider range of consistency or firmness can be achieved than with either the ceramic matrix or collagen matrix alone. Surprisingly, these benefits are achieved while the compositions remain readily injectable, facilitating the preferred use in soft tissue repair and augmentation.

The present invention further comprises methods and kits for preparing such compositions, where the ceramic matrix particles having the requisite size distribution are combined with a fluid carrier and optionally with fibrillar collagen and/or other components. Usually, the kits will comprise prepared compositions in ready-to-use syringes.

The present invention still further comprises methods for using such compositions, wherein the compositions are injected to a soft tissue site, preferably using a needle having a diameter of 20 gauge or smaller. The methods are particularly useful for deep tissue injection to locations near bone and cartilage for purposes such as sphincter repair, nasal repair, and the like.

DESCRIPTION OF THE PREFERRED EMBODIMENT

Figure 1:
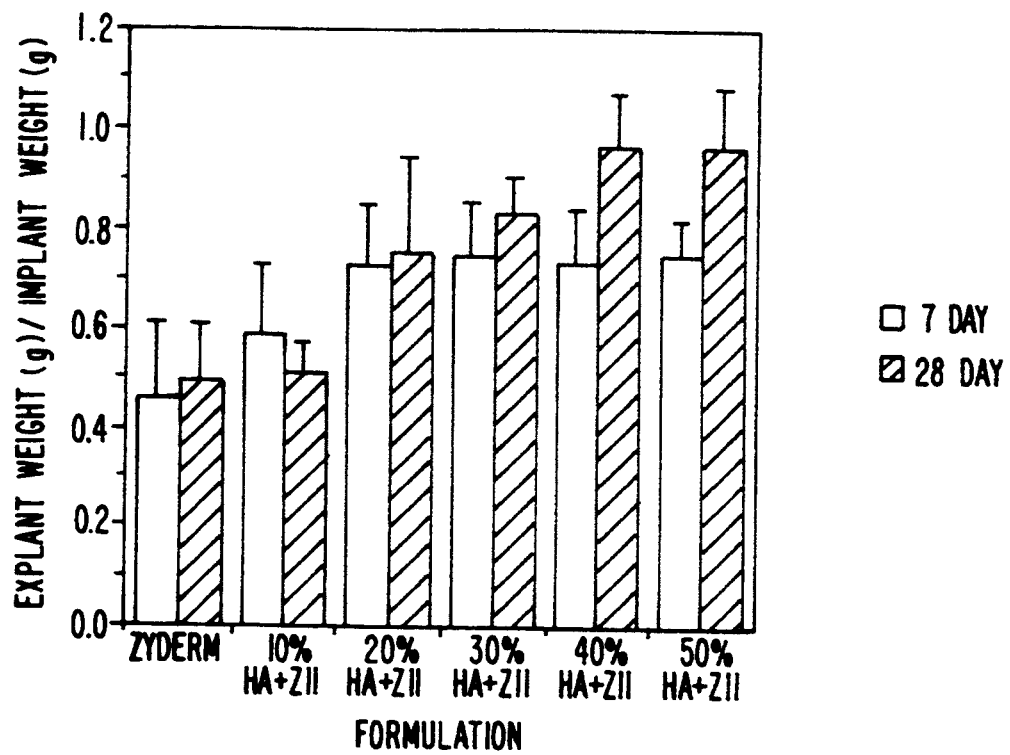
FIG. 1 is a chart comparing the wet weight recovery at various concentrations of hydroxyapatite in Example A of the Experimental section.

Injectable implant compositions according to the present invention are prepared by comminution and size selection of a biocompatible ceramic starting material and incorporation of the resulting sized ceramic particles in a suitable fluid carrier. Optionally, a collagen material and other component(s) may be combined as part of the injectable implant compositions, and the compositions thus formed are useful for a variety of medical purposes, particularly soft tissue implantation and in particular deep tissue implantation to locations near bone, cartilage, and the like.

The sized ceramic particles will form the primary matrix material of the composition of the present invention. By "matrix material," it is meant that the material will persist within a host's tissue at the area of injection for a time sufficient to permit tissue repair or augmentation around and into the material. The fluid carrier will usually be viscous, more usually being a gel, in order to suspend and maximize the concentration of ceramic particles therein. Conveniently, the fluid carrier can be a viscous biocompatible organic polymer, such as polyethylene glycol, hyaluronic acid, poly (hydroxyethyl methacrylate), and the like.

Alternatively, the fluid carrier may comprise a hydrogel, particularly a collagen hydrogel (where the collagen may act both as a carrier and a co-matrix material). In any case, the fluid carrier together with the ceramic matrix particles will form a cohesive mass after injection to the desired tissue site. Overtime, the organic polymer and/or collagen will be resorbed, leaving the ceramic matrix as a supporting structure for the patient's own tissue.

Biocompatible ceramic matrix materials suitable for incorporation into the compositions of the invention may be derived from a variety of calcium phosphate mineral component materials. As used herein, "calcium phosphate mineral" materials refers to those materials composed of $Ca^{+2}$ and phosphate ions, regardless of the microstructure, protonation status of the phosphate, or extent of hydration. Calcium phosphate mineral materials include a variety of forms, such as the commercially available forms of tricalcium phosphate, for example, Synthograft® tricalcium phosphate, or of hydroxyapatite such as Periograf®, Alveograf®, Interpore®, OrthoMatrix™ HA-1000™, or OrthoMatrix™ HA-500™ hydroxyapatite particulate preparations. The hydroxyapatite or tricalcium phosphate may also be prepared by known methods, such as those disclosed by Termine, et al. *Arch Biochem Biophys* (1970) 140:307-325, or by Hayashi et al. *Arch Orthop Trauma Surg* (1982. Supra). In any event, the mineral is generally and preferably of nonbiological origin and is supplied initially as a powder of having an average particle size typically in the range of 100-200 μm, with a maximum size of 1000 μm or larger. While the mineral content of bone could be harvested and purified for this purpose, the use of commercially available calcium phosphate mineral will usually be more economical and preferable, both as a matter of cost and of quality.

The calcium phosphate starting materials will be subjected to conventional size reduction and selection processes to obtain a particle population having a size distribution in the range from 50 μm to 250 μm, preferably being from 100 μm to 200 μm. Particles larger than the upper ranges of these distributions will generally interfere with injectability of the compositions, while particles below the lower ranges of these distributions will be subject to phagocytosis when administered to soft tissue sites. Thus, this size range permits the successful use of the compositions of the present invention for soft tissue repair and augmentation using narrow gauge needle injection techniques. Size distribution can be measured microscopically using an image analyzer.

An exemplary method for size reduction and selection of calcium phosphate particles initially in the 100 μm to 1000 μm size range is set forth in the Experimental section hereinafter. Briefly, a calcium phosphate starting material, such as hydroxyapatite, is crushed into a fine powder having a very broad particle size distribution. The fine powder is wet screened in a device comprising a pair of vertically spaced-apart wire screens where the upper screen has a larger mesh size and the lower screen has a smaller mesh size. In particular, the upper screen is sized to prevent passage of particles larger than those in the desired particle size distribution while the lower screen is sized to permit passage of particles having a smaller particle size than the desired particle size distribution. Thus, the material retained on the upper surface of the lower screen will generally be within the desired particle size distribution.

The collagen component of the composition may be prepared or may be derived from a number of commercially available collagens. Numerous forms of collagen have been prepared and they differ in their physical properties as well as in their biocompatibility. The term, "collagen dispersion" is used herein to refer to a collagen preparation in aqueous medium in which the collagen particle size is not specified, i.e., the preparation may be a solution, suspension, or gel.

Native collagen consists mainly of a triple helical structure containing repeating triplet sequences composed of glycine linked to two additional amino acids, commonly proline and hydroxyproline. Native collagen contains regions at each end which do not have the triplet glycine sequence, and thus do not form helices. These regions are though to be responsible for the immunogenicity associated with most collagen preparations, and the immunogenicity can be mitigated by the removal of these regions to produce "atelopeptide" collagen. This can be accomplished by digestion with proteolytic enzymes, such as trypsin and pepsin. The non-helical telopeptide regions are also responsible for natively occurring cross-linking, and atelopeptide collagen must be cross-linked artificially if cross-linking is desired.

Naturally occurring collagens have been subclassified into about ten types, depending on the amino acid sequence in the individual chains, the carbohydrate content, and the presence or absence of disulfide cross-links. The most common subtypes are Type I, which is present in skin, tendon, and bone, and which is made by fibroblasts; and Type III, which is found primarily in skin. Other types reside in specialized membranes or cartilage, or at cell surfaces. Types I and III contain similar numbers of amino acids in their helices and have a high degree of homology; however, Type III but not Type I, contains two adjacent cysteines at the C-terminal ends of the triple helix, which are capable of forming inter-chain cross-links.

Therefore, collagen preparations may differ from each other by virtue of their initial compositions, which is a function of their origin, or by virtue of their modes of preparation. Collagen derived from bone, for example, contains exclusively Type I collagen; while collagen derived from skin also contains Type III. Also, the process of preparation may or may not remove the telopeptides. Thus both unaltered and "atelopeptide" collagen are possible. Cross-linking may be effected deliberately or accidentally. Sterilization by γ-irradiation or by high heat may result in cross-linking without control of extent or nature and results in partial degradation of the triple helix; deliberate cross-linking may be carried out by a variety of means, including treatment with glutaraldehyde or polyethylene glycol. Differences arising from perhaps more subtle causes are perhaps the result of variations in the details of the preparation procedure. For example, the collagen may be solubilized and reprecipitated, or may simply be finely divided and kept in suspension. When the solubilized material is reaggregated, the aggregation may be done in ways so as to form non-specifically bonded solids, or the collagen may be reconstituted into fibers which simulate the native form. Also, of course, the degree of purity may vary.

As used herein, "free from impurities" or "purified" as regards collagen preparations refers to those impurities which are normally associated with collagen in its native state. Thus, collagen prepared from calfskin is free from impurities when other components of calfskin have been removed; that from bone when other components of bone are eliminated.

"Reconstituted" collagen refers to collagen which has been disassembled into individual triple helical molecules, with or without their telopeptide extensions, brought into solution and then regrouped into "fibrillar" forms. In this form, the fibrils consist of long, thin collagen molecules staggered relative to one another by multiples of about one-fourth their length. This results in a banded structure which can be further aggregated into fibers.

Collagen which is "substantially free from cross-linking" refers to collagen which has had the telopeptides removed, and thus lacks the native capacity for cross-link formation. These preparations remain substantially cross-link free if not deliberately cross-linked by, for example, being treated with chemical crosslinking agents such as glutaraldehyde or subjected to treatment imposing a spurious form of linkage—for example, treatments often used for sterilizing purpose, such as high temperature and γ-radiation.

The preferred collagen for incorporation into the composition of the present invention is a purified atelopeptide fibrillar reconstituted collagen. Non-fibrillar collagen, however, may also be used. Non-fibrillar collagen may be degraded, e.g., by exposure to glycerol and may be maintained in non-fibrillar form at a neutral pH.

One suitable fibrillar collagen preparation is an atelopeptide collagen which is reconstituted into fibrillar form and supplied as a dispersion of 5–100 mg/ml, preferably around 50–70 mg/ml. Such dispersions as Zyderm® Collagen Implant (ZCI), which is commercially available in preparations containing 35 or 65 mg/ml collagen in saline, manufactured by Collagen Corporation, Palo Alto, Calif., are appropriate. For use in the compositions of the inventions, the ZCI or other collagen dispersions are used without lidocaine or other sedative drugs. As used herein, "ZCI" refers to the aqueous collagen dispersion, rather than to the collagen component per se.

The ceramic matrix particles and optionally the collagen component of the present invention will be combined in a suitable fluid carrier, typically a buffered aqueous media (pH 7.0 to 7.4). In the case of compositions which do not include a collagen component, the fluid carrier will typically consist of or further comprise a viscous organic polymer base material, such as polyethylene glycol, hyaluronic acid, poly (hydroxyethylene methacrylic acid) or the like. The organic polymer base does not act as a matrix material, i.e., it is not persistent and is quickly lost from a site of tissue administration leaving the ceramic particle matrix in place as the matrix. Instead, the organic polymer base acts to maintain the ceramic matrix particles in suspension and to form a cohesive mass at the injection site. Some organic polymers, such as polyethylene glycol, may also act as a lubricant. A preferred organic polymer is polyethylene glycol, particular having a molecular weight from 400 to 20,000. The polyethylene glycol may be part of an aqueous solution or may be used without water.

The organic polymer base material is present in the ceramic implant compositions at a concentration from about 0.1% to 20% (weight basis), usually from about 0.5% to 10%, and preferably from about 0.5% to 5%.

In the case of the implant compositions which also include a collagen component, the addition of an organic polymer base is usually not necessary (although its presence is not intended to be excluded). The collagen in such compositions will typically be present at a concentration of at least 1% by weight, usually being present at from 1% to 20% by weight, and more usually being present at from 1% to 10% by weight. The persistence and texture of the implant composition can be controlled by adjusting the weight ratio of ceramic material to collagen, with higher amounts of ceramic corresponding to firmer, more persistent implants. Usually, the weight ratio will be in the range from about 1:19 to 1:1 (ceramic matrix: collagen), usually being in the range from about 1:9 to 1:1.5, and preferably being in the range from about 1:4 to 1:2.

It is important that the total solids content and viscosity of the compositions of the present invention be within a range which permits injection of the compositions through relatively narrow gauge needles, usually 20 gauge or higher, preferably 22 gauge or higher. The total solids content, including ceramics matrix particles, collagen, organic polymer, and the like, will usually be in the range from 60% (weight basis) to 4%, usually being in the range from 20% to 50%, and preferably being in the range from about 35% to 40%. The corresponding viscosities will usually be in the range from about 0.4 Pa/sec to 0.005 Pa/sec, usually being in the range from about 0.3 Pa/sec to 0.05 Pa/sec, and preferably being in the range from about 0.2 Pa/sec to 0.1 Pa/sec.

The compositions of the present invention may further include biocompatible fluid lubricants and/or viscosity modifiers, generally as described in U.S. Pat. No. 4,803,075, the disclosure of which is incorporated herein by reference. Exemplary lubricant components include glycerol, glycogen, maltose, and the like. Organic polymer base materials, such as polyethylene glycol and hyaluronic acid as well as non-fibrillar collagen, preferably succinylated collagen, may also act as lubricants. Such lubricants generally act to enhance the intrudability into soft tissue and improve the injectability by modifying the viscosity of the compositions.

When used for hard tissue and bone implantation and repair, the compositions of the present invention may include additional components, such as osteogenic factors, as described generally in U.S. Pat. Nos. 4,888,366; 4,863,732; and 5,001,169, the disclosures of which are incorporated herein by reference. The compositions may also include autologous bone marrow, as generally described in U.S. Pat. No. 4,774,227, the disclosure of which is incorporated herein by reference.

In a preferred aspect of the present invention, biologically active substances (other than collagen), such as proteins and drugs, may be incorporated in the compositions to provide for controlled release of these active substances after injection of the compositions. Hydroxyapatite particles within the compositions of the present invention have a generally negative charge which can interact with positively charged proteins, drugs, and the like. In particular, the hydroxyapatite can interact with amino groups on a protein substance which is desired to be delivered to the host. Exemplary proteins would include tissue growth factors, such as TGF-$\beta$, and the like which would promote healing and tissue repair at the site of injection. Compositions of the present invention would be useful for delivering substances other than growth promotants, and would therefore be useful for the controlled delivery of a wide variety of positively charged drug and proteins for purposes other than tissue repair and augmentation.

The components of the ceramic implant material of the present invention may be combined in any manner which provides for a homogeneous mixture. For example, components may be mixed homogeneously by repeated passage through pumps or repeated transfer between adjacent syringes having a small diameter interconnecting channel. A suitable syringe device providing the necessary mixing as described in U.S. Pat. No. 4,743,229, the disclosure of which is incorporated herein by reference.

The injectable ceramic implant compositions of the present invention may be injected intradermally or subcutaneously into humans or other mammals to augment soft tissue, to repair tissue defects, to correct congenital anomalies, to correct cosmetic defects, and the like. The compositions of the present invention may also be injected into internal tissues, such as the tissues defining body sphincters to augment such tissues. See, in particular, copending applications Ser. No. 07/843,124 (Attorney Docket No. 05921-10) and Ser. No. 07/843,379 (Attorney Docket No. 05921-12), the disclosures of which are incorporated herein by reference. Specific uses of the implant compositions of the present invention are described in detail in the above patents and patent applications which have been incorporated herein by reference.

The injectable ceramic implant compositions of the present invention may also be used for repair or augmentation of hard tissues, such as bone, cartilage, connective tissues, and the like. The injectability of the compositions remains a particular benefit when they are being used in such hard tissue applications. Hard tissue and bone augmentation and repair are described generally in U.S. Pat. Nos. 5,001,169; 4,863,732; 4,563,350, the disclosures of which are incorporated herein by reference.

The compositions of the present invention may be stored as a kit, where the separate components (i.e., the ceramic matrix, the fluid carrier, the collagen (if present), and other optional components are packaged in a ready-to-use syringe.

The following example is offered by way of illustration, not by way of limitation.

EXPERIMENTAL

Material Preparation

Sterile, non-pyrogenic hydroxyapatite (HA), having more rounded edges, of particle size 140–160 $\mu$m, was obtained from Lifecore Biomedical. Samples of the material were placed on a microscope slide, and the particle size distribution determined using image analysis.

The ceramic particles (average particle size 179 $\mu$m) were aseptically mixed with Zyderm®II Collagen Implant (ZCI) to concentrations of 10% and 30% ceramic, by weight, to form the collagen ceramic implants.

ZCI samples containing 10% ceramic or 30% ceramic were evaluated in subcutaneous tissue in rats. Approximately 0.25 cc samples were injected bilaterally in the suprascapular subcutis of Sprague-Dawley rats. At 14 and 28 days post-implantation, the implants were exposed and dissected free of the surrounding connective tissue. The total wet weight of the explant was determined, and each explant was evaluated histologically.

Histology Conclusion

Histology data reveal information relating to the implant's biocompatibility. The responses to all the test materials at 14 days were within the normal range of biocompatibility. However, calcification was seen in some of the implants. At day 28, all implants were reasonably biocompatible, except the ZCI containing 30% HA, which had marginal biocompatibility. Many of the implants containing HA were showing signs of calcification; however, some calcification is typical in the rat subcutaneous model. None of the HA-containing implants showed granuloma formation, which is often seen in injectable particulate-containing compositions, such as Polytef® paste or Bioplastique ™.

Wet Weight Persistence

Figure 2:
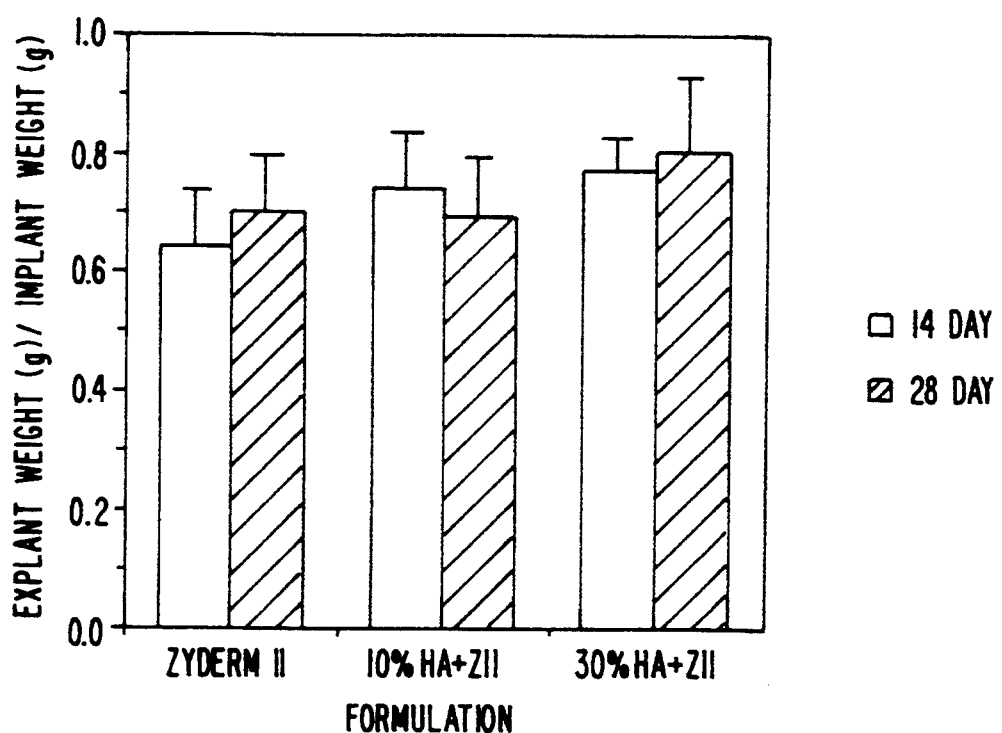
FIG. 2 is a chart comparing the wet weight recovery at various concentrations of hydroxyapatite in Example B of the Experimental section.

Wet weight recovery is a measure of the implant's persistence. Wet weight recovery of the implant was constant in all formulations over 28 days. The recovery was slightly higher for the ZCI containing 30% HA. See FIG. 2.

Although the foregoing invention has been described in detail for purposes of clarity of understanding, it will be obvious that certain modifications may be practiced within the scope of the appended claims.

What is claimed is:

1. An injectable implant composition comprising collagen and biocompatible ceramic particles present in a pharmaceutically acceptable fluid carrier, wherein the ceramic particles have been size selected to have a size distribution in the range from 50 $\mu$m to 250 $\mu$m.

2. An injectable implant composition as in claim 1, wherein the ceramic particles are composed of calcium phosphate mineral.

3. An injectable implant composition as in claim 2, wherein the calcium phosphate mineral is selected from the group consisting of sintered hydroxyapatite and tricalcium phosphate.

4. A method for preparing injectable implant compositions, said method comprising combining ceramic particles and collagen in a pharmaceutically acceptable fluid carrier, wherein the ceramic particles have been size selected to have a size distribution in the range from 50 $\mu$m to 250 $\mu$m.

5. A method as in claim 4, wherein the ceramic particles are composed of calcium phosphate mineral particles.

6. A method as in claim 4, wherein the calcium phosphate mineral particles are composed of a material selected from the group consisting of sintered hydroxyapatite and tricalcium phosphate.

7. A method as in claim 4, wherein the fluid carrier comprises a biocompatible organic polymer which will dissipate from a tissue injection site, leaving the mineral particles.

8. A method as in claim 7, wherein the organic polymer is a polyethylene glycol.

9. A kit comprising:

a syringe loaded with a volume of collagen and biocompatible ceramic particles which have been size selected to have a size distribution in the range from 50 $\mu$m to 250 $\mu$m present in a fluid carrier.

10. A method for preparing injectable implant compositions, said method comprising:
providing a ceramic material in the form of a fine powder;
screening the fine powder to remove ceramic particles sized above 250 $\mu$m and below 50 $\mu$m; and
combining the fine powder remaining after screening with collagen and a pharmaceutically acceptable fluid carrier.

11. A method as in claim 10, wherein the ceramic powder is treated to enhance surface porosity prior to combination with the fluid carrier.

12. A method as in claim 10, wherein the ceramic powder is composed of calcium phosphate mineral particles.

13. A method as in claim 12, wherein the calcium phosphate mineral particles are composed of a material selected from the group consisting of sintered hydroxyapatite and tricalcium phosphate.

14. A method as in claim 10, wherein the ceramic powder is combined in the fluid carrier at a concentration from 0.75 gm/ml to 0.05 gm/ml.

15. A method as in claim 10, wherein the fluid carrier comprises a biocompatible organic polymer which will dissipate from a tissue injection site, leaving the mineral particles.

16. A method as in claim 15, wherein the organic polymer is a polyethylene glycol.

17. A method as in claim 10, wherein the ceramic powder and the collagen are combined at a weight ratio in the range from 1:19 to 1:1 ceramic powder: collagen.

18. A method as in claim 10, further comprising combining the pharmaceutically acceptable fluid carrier with a biocompatible fluid lubricant.

19. A method as in claim 18, wherein the biocompatible fluid lubricant is glycerol of succinylated collagen.

20. A method as in claim 10, further comprising combining at least one biologically active substance.

21. A method as in claim 20, wherein the substance is selected from the group consisting of tissue growth factors, osteogenic factors, and bone marrow.

22. An injectable implant composition comprising collagen and ceramic particles composed of calcium phosphate mineral and having enhanced surface porosity present in a pharmaceutically acceptable fluid carrier, wherein the ceramic particles have been size selected to have a size distribution in the range from 50 $\mu$m to 250 $\mu$m.

23. An injectable implant composition comprising collagen and biocompatible ceramic particles present in a pharmaceutically acceptable fluid carrier at a concentration from 0.75 gm/ml to 0.05 gm/ml, wherein the ceramic particles have been size selected to have a size distribution in the range from 50 $\mu$m to 250 $\mu$m.

24. An injectable implant composition comprising collagen and biocompatible ceramic particles present in a biocompatible organic polymer which will dissipate from a tissue injection site leaving the ceramic particles and collagen, wherein the ceramic particles have been size selected to have a size distribution in the range from 50 $\mu$m to 250 $\mu$m.

25. An injectable implant composition a in claim 24, wherein the organic polymer is polyethylene glycol.

26. An injectable implant composition comprising collagen and biocompatible ceramic particles present in a pharmaceutically acceptable fluid carrier at a weight ratio in the range from 1:19 to 1:1 ceramic particles: collagen, wherein the ceramic particles have been size selected to have a size distribution in the range from 50 μm to 250 μm.

27. An injectable implant composition comprising collagen, biocompatible ceramic particles, and a biocompatible fluid lubricant, present in a pharmaceutically acceptable fluid carrier, wherein the ceramic particles have been size selected to have a size distribution in the range from 50 μm to 250 μm.

28. An injectable implant composition as in claim 27, wherein the biocompatible lubricant is glycerol or succinylated collagen.

29. An injectable implant composition comprising collagen, biocompatible ceramic particles, and at least one biologically active substance present in a pharmaceutically acceptable fluid carrier, wherein the ceramic particles have been size selected to have a size distribution in the range from 50 μm to 250 μm.

30. An injectable implant composition as in claim 29 wherein the biologically active substance is a tissue growth factor, an osteogenic factor, or bone marrow.

31. An method for preparing injectable implant compositions, said method comprising combining ceramic particles and collagen in a pharmaceutically acceptable fluid carrier wherein the ceramic particles have been treated to enhance surface porosity prior to combining and have been size selected to have a size from 50 μm to 250 μm.

32. A method for preparing injectable implant compositions, said method comprising combining ceramic particles and collagen in a pharmaceutically acceptable fluid carrier at a concentration from 0.75 gm/ml to 0.05 gm/ml, wherein the ceramic particles have been size selected to have a size from 50 μm to 250 μm.

33. A method for preparing injectable implant compositions, said method comprising combining ceramic particles and collagen in a pharmaceutically acceptable fluid carrier at a weight ratio in the range from 1:19 to 1:1 ceramic particles: collagen, wherein the ceramic particles have been size selected to have a size from 50 μm to 250 μm.

34. A method for preparing injectable implant-compositions, said method comprising combining ceramic particles, collagen, and a biocompatible fluid lubricant in a pharmaceutically acceptable fluid carrier, wherein the ceramic particles have been size selected to have a size from 50 μm to 250 μm.

35. A method as in claim 34, wherein the biocompatible fluid lubricant is glycerol or succinylated collagen.

36. A method for preparing injectable implant compositions comprising combining ceramic particles, collagen, and at least one biologically active substance, in a pharmaceutically acceptable fluid carrier, wherein the ceramic particles have been size selected to have a size from 50 μm to 250 μm.

37. A method as in claim 36, wherein the biologically active substance is selected from the group consisting of tissue growth factors, osteogenic factors, and bone marrow.

* * * * *